(12) United States Patent
Fitzgerald et al.

(10) Patent No.: US 10,327,742 B2
(45) Date of Patent: Jun. 25, 2019

(54) CELL SAMPLING DEVICE

(75) Inventors: Rebecca C. Fitzgerald, Cambridge (GB); Suni Sudarshan R. Kadri, Cambridge (GB); Pierre Lao-Sirieix, Cambridge (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 1111 days.

(21) Appl. No.: 13/509,035

(22) PCT Filed: Nov. 11, 2010

(86) PCT No.: PCT/GB2010/002077
§ 371 (c)(1),
(2), (4) Date: May 10, 2012

(87) PCT Pub. No.: WO2011/058316
PCT Pub. Date: May 19, 2011

(65) Prior Publication Data
US 2012/0226189 A1    Sep. 6, 2012

(30) Foreign Application Priority Data

Nov. 13, 2009    (GB) .................................. 0920014.8

(51) Int. Cl.
    *A61B 10/02*    (2006.01)
    *A61B 5/00*    (2006.01)

(52) U.S. Cl.
    CPC ............ *A61B 10/02* (2013.01); *A61B 5/4233* (2013.01); *A61B 2010/0216* (2013.01)

(58) Field of Classification Search
None
See application file for complete search history.

(56) References Cited

U.S. PATENT DOCUMENTS

| | | | |
|---|---|---|---|
| 3,528,429 A | 9/1970 | Beal et al. | |
| 3,593,369 A * | 7/1971 | Anderson et al. | 452/134 |
| 3,795,948 A * | 3/1974 | Kapitan | 24/114.7 |
| 4,735,214 A | 4/1988 | Berman | |
| 5,749,879 A * | 5/1998 | Middleman et al. | 606/139 |
| 5,772,542 A * | 6/1998 | Gildea et al. | 473/576 |
| 6,428,964 B1 * | 8/2002 | Shuber | 435/6.14 |
| 7,371,527 B1 * | 5/2008 | Baylin et al. | 435/6.12 |
| 8,709,736 B2 * | 4/2014 | Lao-Sirieix et al. | 435/7.21 |
| 2001/0036635 A1 * | 11/2001 | Waldman et al. | 435/6 |
| 2003/0130235 A1 * | 7/2003 | Mattson et al. | 514/80 |
| 2003/0234523 A1 * | 12/2003 | Henderson et al. | 280/730.2 |
| 2004/0033502 A1 * | 2/2004 | Williams et al. | 435/6 |

(Continued)

FOREIGN PATENT DOCUMENTS

WO    WO 2007/045896 A1    4/2007

OTHER PUBLICATIONS

International Search Report dated Mar. 25, 2011.
(Continued)

*Primary Examiner* — Matthew Kremer

(57) ABSTRACT

A swallowable cell sampling device comprising an abrasive material capable of collecting cells from the surface of the oesophagus is described. The swallowable cell sampling device may include an apparatus for retrieval comprising a cord. Moreover, the cord may be attached to the abrasive material with a hitch knot. Additionally, kits and methods involving the same are described.

16 Claims, 3 Drawing Sheets

(56) References Cited

U.S. PATENT DOCUMENTS

| | | | |
|---|---|---|---|
| 2004/0146907 A1* | 7/2004 | Smith | 435/6 |
| 2005/0177938 A1* | 8/2005 | Steiner | 5/121 |
| 2006/0189898 A1* | 8/2006 | Nitzan et al. | 600/587 |
| 2008/0058584 A1* | 3/2008 | Hirotsuka et al. | 600/37 |
| 2009/0023997 A1* | 1/2009 | Stokes et al. | 600/116 |

OTHER PUBLICATIONS

Dellmar: "A Secure Arthroscopic Knot" Database Medline [Online], U.S. National Library of Medicine (NLM), Bethesda, MD. US; Jun. 1996 (Jun. 1996), XP002627658, Database accession No. NLM8783832 *abstract.
Communication pursuant to Article 94(3) EPC for Application No. 10796447.0 dated May 26, 2015 from the European Patent Office.
Communication pursuant to Article 94(3) EPC for Application No. 12809298.8 from the European Patent Office dated Sep. 14, 2015.

* cited by examiner

CELL SAMPLING DEVICE

FIELD OF THE INVENTION

The invention relates to a cell collection device. In particular, the invention relates to a cell collection device for sampling cells lining the oesophagus.

BACKGROUND TO THE INVENTION

Certain cell collection devices are known. In particular, a capsule sponge type cell collection device is described in PCT patent application number PCT/GB2006/003913. Such a device comprises an abrasive material capable of collecting cells from the surface of the oesophagus, together with means for its retrieval from the patient. Typically such devices are swallowable.

Known devices typically operate by swallowing the abrasive material in a compressed or stowed format. Upon reaching the stomach cavity, the material retaining the device in a compressed or stowed format is dissolved or weakened, permitting expansion of the compressed material back to its original size. Following this stage the device is then retrieved by physically pulling it from the subject's mouth. This pulling causes the device to travel out of the stomach cavity back up through the oesophagus and out through the patient's buccal cavity and mouth. In travelling along the subject's oesophagus, cells from the oesophageal lining are collected in the abrasive material part of the device. These cells are subsequently analysed to aid in the diagnosis or prognosis for the subject.

One known cell sampling device as described above is referred to as a capsule sponge. This device comprises a compressible sponge like material. This is typically attached to a cotton thread. The device is then compressed into a swallowable form, such as by incorporation into a gelatine capsule. Such known devices have typically had a cotton cord attached as the means of retrieval. This is a problem since cotton cords can shed fibres inside the subject. Moreover, cotton cord of thus type can be too rough. In addition, material may detach from the cord during use. Furthermore, the known device has suffered from the problem of loss inside the subject being sampled. This has typically occurred via separation of the uncompressed device from the cord for its retrieval. Furthermore, the known devices can be difficult to swallow due to friction of the cord on the oropharynx.

Thus, known cell sampling devices suffer from a range of problems and drawbacks. The present invention seeks to overcome problems associated with the prior art.

SUMMARY OF THE INVENTION

The present inventors provide improvement on the known cell collection devices. The inventors have employed different cords or threads attached to the compressible abrasive material of the device in order to improve swallowability and ease of use of the device. Furthermore, the inventors have designed a new attachment system for the cord attachment to the abrasive material. This attachment system comprises certain specific classes of knot that provide superior strength. Furthermore, the knots used are advantageously shown to reduce losses of the device in the subjects during use. Thus, the invention provides a stronger and safer cell sampling device. The device also enjoys benefits of superior swallowability and ease of use/retrieval.

Thus in one aspect the invention provides a swallowable cell sampling device comprising an abrasive material capable of collecting cells from the surface of the oesophagus, and a means for retrieval wherein the means for retrieval comprises a cord characterised in that the cord is attached to the abrasive material by means of a hitch knot.

Suitably said hitch knot is a double overhand knot.

Suitably said abrasive material is compressible.

Suitably said abrasive material comprises reticulated polyurethane.

Suitably said cord is attached to said abrasive material via a loop of cord arranged below the surface of the abrasive material, said loop being closed by the hitch knot.

Suitably said abrasive material is compressed and wherein said abrasive material is retained in a compressed state by a soluble capsule.

Suitably said soluble capsule comprises a gelatine capsule.

Suitably said capsule is capable of dissolution and the compressible abrasive material is capable of reverting to its uncompressed size within 5 minutes upon immersion in water at 30 degrees Celsius.

Suitably the device comprises an unswallowable element at the end distal from the swallowable abrasive material.

In another aspect, the invention relates to a kit comprising a device according to any preceding claim, and reagent for use in the detection of a cellular marker.

In another aspect, the invention relates to a method for aiding the diagnosis of Barrett's oesophagus or Barrett's associated dysplasia in a subject, said method comprising sampling the cellular surface of the oesophagus of said subject with a device as described above, and assaying the cells for a cellular marker, wherein detection of such a marker indicates increased likelihood of the presence of Barrett's or Barrett's associated dysplasia.

A kit as described above or a method as described above wherein the marker is selected from the group presented in Table 1.

A kit as described above or a method as described above wherein the marker is selected from the group presented in Table 2.

A kit as described above or a method as described above wherein the marker is selected from the group presented in Table 3.

DETAILED DESCRIPTION OF THE INVENTION

A preferred embodiment of the invention is a 'capsule sponge' device where the abrasive material comprises a sponge or sponge like material such as polyurethane mesh and wherein said material is packed or compressed into a gelatine capsule for ease of swallowing. Thus the generic term 'sponge' or 'capsule sponge' is sometimes used to discuss the device of the invention for ease of understanding but it will be apparent that other embodiments of the invention are envisaged and that the invention is not to be understood as limited only to preferred capsule sponge embodiment(s).

The term 'comprises' (comprise, comprising) should be understood to have its normal meaning in the art, i.e. that the stated feature or group of features is included, but that the term does not exclude any other stated feature or group of features from also being present.

Retrieval

The device of the invention suitably comprises means for retrieval from the subject being sampled. Suitably the means for retrieval may comprise a cord. The cord is occasionally referred to herein as thread/string.

The cord used should suitably be slippery. By slippery it is meant having a low co-efficient of friction. This has the advantage of easing the swallowing of the device. This has the further advantage of easing retrieval of the device. A further advantage is to reduce discomfort to the patient during use. By low co-efficient of friction is meant a co-efficient of friction which is lower than that of a cotton cord of similar diameter.

The cord used should suitably be smooth. This has the advantage of being easier to swallow. This has the further advantage of avoiding sticking to the mucosa in the mouth, throat or oropharynx.

Dimensions

Suitably the cord or thread should be selected so as to avoid injury to the oropharynx of the subject during use. Thus, in one aspect the invention relates to a new use of surgical thread which has formerly been applied only as suture material. Suture material is an example of a suitable cord for use in the present invention. Suitably the thinnest possible cord is used, whilst remaining thick enough to avoid cutting the patient during use.

Attention should be paid to choosing the correct thickness of the cord. Too thick a cord can be difficult to swallow, yet too thin can cause laceration to the throat.

The cord should suitably be suitably thick to avoid cutting the patient during use. Thus suitably the cord has a minimum diameter of at least 0.3 mm.

The cord should be suitably thin in order to minimise discomfort and improve swallowability. Thus suitably the cord has a maximum diameter of 0.7 mm.

Thus, the cord which may be used according to the present invention suitably comprises a cord having a diameter in the range 0.3 to 0.7 mm, more suitably in the range 0.4 to 0.6 mm. A most suitable cord diameter is approximately 0.5 mm, most suitably 0.5 mm.

It should be noted that values given for cord diameters herein are of course subject to usual measurement tolerances. In particular the figures given should be allowed a tolerance of +/−0.05 mm. Thus a size of 0.5 mm should be understood to embrace 0.45-0.55 mm with the tolerance noted.

The length of the cord is matter for the operator. The cord needs to be long enough to allow deployment of the device into the subject's stomach cavity whilst retaining enough cord extending into the buccal cavity or beyond to allow commencement of retrieval. Thus the optimal cord length is the distance from the buccal cavity to the stomach cavity plus an extra length such as 5 cm to permit grasping and retrieval of the device. Longer cords may be advantageous to provide ease of withdrawal and/or to provide reassurance to the subject.

Suitably the cord is at least 60 cm long. Suitably the cord is less than 75 cm long.

Suitably the cord is in the range 60-75 cm, suitably 64-69 cm, suitably about 67 cm long, suitably 67 cm long.

Strength

The cord must be chosen to have the strength necessary to prevent against breakage upon withdrawal.

Suitably the cord is break resistant to a load of at least 2.4 Kg, suitably to at least 3.2 Kg, suitably to at least 3.5 Kg, suitably to at least 4.6 Kg.

Further Properties

Suitably the thread or cord used is of pale colour such as white. This has the advantage of being preferred by subjects.

Suitably the abrasive material or capsule used is of dark colour such as black. This has the advantage of being preferred by subjects during use. This has the further advantage of disguising or making less prominent the appearance of any biopsy material trapped on the abrasive part of the device once retrieved from the subject. This can assist in reducing distress in the subject during operation.

Suitably the cord comprises a cord suitable for internal use. Suitably the cord comprises a cord certified for internal use. Certified means approved by a relevant health authority such as the UK MHRA (Medicines and Healthcare products Regulatory Agency). Suitably the cord should not shed fibres inside the subject. Suitably the cord should display no loss of material from cord into the digestive system of the subject.

The cord may comprise surgical suture material.

At the non-cell-collecting end, suitably the cord is tethered to an anchor to prevent swallowing. Suitably the anchor may comprise cardboard.

Attachment

The means for retrieval (such as a cord) must be attached to the cell sampling abrasive material of the device. It is a key teaching of the present invention that a particular knot system is used to attach the cord to the abrasive element of the device.

Suitably a double half knot should be used. An example of a particularly suitable double half knot is a double overhand knot. This type of knot arrangement provides the advantage that the first half knot falls onto or presses against the second half knot. This is advantageous because the more force that is applied to the cord during retrieval, the more the knot tends to tighten (rather than loosening).

An advantage of the knot system used in the invention is that the cord is attached to the abrasive material via a loop. This loop may reduce in size with the force applied. Clearly, reduction of the size of the loop will partially constrict or compress the internal part of the abrasive material. Importantly however, this knot arrangement does not significantly reduce the diameter of the abrasive material. In particular, this loop arrangement does not significantly decrease the lateral diameter of the abrasive material. By lateral diameter is meant the diameter in the axis perpendicular to the force applied by the cord during retrieval. This has the advantage that, although the shape of the abrasive material may change slightly during constriction of the loop under the force of retrieval, the lateral diameter of the abrasive material remains substantially constant and therefore remains effective in sampling the cells of the oesophagus during retrieval.

The knot attaching the cord to the sponge optimised for:

Numerous knots were investigated that for use with slippery cord material including material which can become more slippery when wet e.g. when mixed with mucous from the mouth or stomach.

Multiple knots may be used. Suitably only a single knot is used, which has the advantage of simplifying construction of the device. Of course a single knot may comprise multiple hitches or elements and refers to a single entire knot rather than a single thread element within an individual knot.

Suitably the knot of the device has one or more of the following properties:

(i) The knot of the invention is suitably tightened under tension to prevent detachment of the sponge from the cord upon removal.

(ii) The knot suitably does not affect significantly the external diameter of the abrasive material such as sponge when under tension.

(iii) The knot suitably does not leave an overhang loop of cord material at the bottom of the abrasive material such as sponge.

Suitably the knot of the device has two or more of said properties; suitably the knot of the device has all three of said properties.

Examples of classes of knot, and of specific knots, having these properties are discussed below.

Two Half Hitch Knot

The two half-hitches is a type of knot, specifically a binding knot or hitch knot. It consists of an overhand knot tied around a post, followed by a half-hitch. Equivalently, it consists of a half-turn around a post followed by a clove hitch of the running end around the standing part.

This knot is also sometimes referred to as a clove hitch over itself.

The person skilled in the art will be familiar with the standard knot names and terminology used herein and will therefore be able to tie them without further guidance. Nevertheless, the following three-step process for tying the two half-hitches is provided for ease of understanding:

Begin by forming a clockwise loop around the pole, with the working end of the rope on top. Bring the working end through the loop. At this point, you have an overhand knot around the pole.

Bring the working end down and to the left. Loop it under the standing end. Pull the working end through the loop just formed, tighten, and slide the knot along the standing end up to the post.

A correctly tied two half hitches resembles a clove hitch tied around the standing end of the line, not a cow hitch.

In discussion of knots presented herein, the context of the device must be borne in mind. For example, there is clearly no 'pole' incorporated into the device of the invention. The 'pole' is merely a common point of explanation for knot tying and in the context of the invention should be understood to be the material around which the knot is being tied, such as the centre of core of the abrasive material (when the cord suitably runs under the surface of the material therefore passing around the inner part of the abrasive material collector part of the device.)

Alternate Knots

Suitably one or more of the following knots may be used for attachment: Anchor hitch knot (this is an alteration in hitch knot).

Suitably the knot is a hitch knot.

All types of hitch knots can potentially be used for attachment, except single hitch knots which are not suitable. It will be borne in mind that some of the hitch knots are complex and therefore are less desirable and/or less practical for manufacture. Suitably the knot is a simple hitch knot, which has the advantage of ease of manufacture.

Alternate Hitch Knots alternate ring hitching, anchor bend variant, bale sling hitch, barrel hitch, becket hitch, blackwall hitch, blake's hitch, boom hitch, bottom loaded release hitch, buntline hitch, cat's paw, chain hitch, clinging clara, clove hitch, continuous ring hitching, cow hitch variant, cow hitch with toggle, cow hitch, double half hitches, Farrimond friction hitch, garda hitch, ground-line hitch, half hitch, halter hitch, highpoint hitch, highwayman's hitch, hitching tie, icicle hitch, killick hitch, knute hitch, lighterman's hitch, magnus hitch, marline hitching, marlinespike hitch, masthead knot, midshipman's hitch, munter hitch, munter friction hitch, ossel hitch, palomar knot, pile hitch, prusik knot, reverse half hitches, round hitch, round turn and two half hitches, sailor's gripping hitch, sailor's hitch, siberian hitch, single hitch, slippery hitch, snell knot, snuggle hitch, taut-line hitch, timber hitch, trilene knot, trucker's hitch, tugboat hitch, uni knot, wagoner's hitch Most suitably said hitch knot is a double overhand knot. This has the advantage of ease of tying. This knot has each of the properties (i) (ii) and (iii) given above. Further advantages may be apparent from the examples section of the application.

Double loop bow line knot is suitably not used in the invention, suitably the attachment does not comprise a double loop bow line knot.

Known devices have not used the knot systems described herein. Known devices have only used full knots rather than half knots. In particular, known devices have used multiple "granny knots" and have not used the slidable noose system for attachment as described herein.

Free End

The free end of the cord refers to the free part after the knot at the cell collector end of the cord. Suitably the free end is at least 1 cm. Suitably the free end is in the range 1.0-2.0 cm. Suitably the free end may be at least 1.5 cm, suitably at least 1.7 cm, suitably 2.0 cm.

Problematic Knots

Unsuitable knots include a Sheet Bend—this knot should not be used as it is slippery and may not withstand the pulling force on the cord; Double sheet bend should not be used as it is slippery and may not withstand the pulling force on the cord and can also be complex to perform; Reef Knot should not be used on slippery threads/cords; Clove hitch is a knot for a looping thread or cord, not for a single free end thread or cord, and leaves two threads at the free end which is not acceptable for the device of the invention and so suitably the clove hitch should not be used. In addition to the above, it should be noted that a Bow Line knot is slippery; structure of this knot is similar to a sheet bend; thus the bow line knot is suitably avoided. Thus suitably the attachment to the abrasive material does not comprise a knot mentioned in this paragraph.

Attachment at Non-swallowed End

It will be noted that the discussion of attachment and knots refers to the joining of the abrasive material to the cord. The non-abrasive-material end of the cord (i.e. the non-swallowed end) may be joined to a further element for example to prevent accidental swallowing, to facilitate withdrawal or for any other purpose. The joining of the cord at the non-swallowed end may be by any suitable means such as welding, stitching, stapling, weaving, gluing or any other method including knotting but when joined by knotting the knot may be any suitable knot for secure fastening and need not be restricted in the manner described as part of the invention for joining of the cord to the abrasive material.

Abrasive Material/Capsule

The abrasive material suitably comprises a sponge or sponge like material.

The qualities of the abrasive material are discussed in more detail below. A key feature is that the material needs to be abrasive enough to collect as many cells as possible whilst at the same time avoiding damage to the oesophagal lining. These advantageous features may be achieved for example via use of a sponge or honeycomb form of abrasive material. This porous or cavitated form of material maximises collection and/or entrapment of cells inside and on the surface of material. Moreover, the cavities or hollows in sponge like or honeycomb material such as reticulated polyurethane also facilitate compression which is advantageous in reducing the size of the material at administration for example via a soluble capsule.

Suitably the material has a uniform shape.

Suitably the material has a uniform diameter.

Suitably the uncompressed shape is round such as spherical.

Suitably the uncompressed diameter is 3 cm.

Suitably the material is dimensioned to fit into a swallowable capsule such as a gelatine capsule, suitably in a compressed or stowed form. Suitably said material does not break the capsule whilst compressed inside, but only deforms or breaks the capsule once in use such as inside the subject.

Suitably the capsule has a uniform shape.

Suitably the capsule has a uniform size.

Suitably the capsule dissolves quickly such as dissolves in 30 degree centigrade water within 5 minutes.

Suitably said capsule is intact all over and does not have any breaks and sharp ends.

This has the advantage of preventing injury while swallowing.

Further Advantageous Features

Suitably the device of the invention may be irradiated for cleanliness.

Suitably the device of the invention may be irradiated for sterility.

In a most preferred embodiment the device has the following properties:

White colour cord

Minimum length of cord—60 cms

Cord smooth on the surface

Cord loop inside the cell collecting abrasive material such as sponge—should loop just below the surface Free end of the cord after the knot at cell collector end—minimum of 1 cm Attachment of cord to cell collector via Knot—Double hitch knot Cord Break resistant—Minimum requirement of 2.4 kg Cord tethered to cardboard at non-cell-collector end to prevent swallowing In another aspect, the invention relates to a method for aiding the diagnosis of Barrett's oesophagus or Barrett's associated dysplasia in a subject, said method comprising sampling the cellular surface of the oesophagus of said subject, and assaying the cells for a cellular marker, wherein detection of such a marker indicates increased likelihood of the presence of Barrett's or Barrett's associated dysplasia. Preferably said sampling is not directed to a particular site within the oesophagus. Preferably only the surface of the oesophagus is sampled. This has the advantage of avoiding more invasive sampling techniques such as biopsy collection techniques which penetrate below the surface of the oesophagus.

In another aspect, the invention relates to a non-invasive method for aiding the diagnosis of Barrett's oesophagus or Barrett's associated dysplasia, comprising assaying cells from the surface of a subject's oesophagus for a cellular marker, wherein detection of such a marker indicates increased likelihood of the presence of Barrett's or Barrett's associated dysplasia. In this embodiment, preferably the actual sampling of the cells is not part of the method of the invention.

In another aspect, the invention relates to a method for aiding the diagnosis of squamous cell carcinoma in a subject, said method comprising sampling the cellular surface of the oesophagus of said subject, and assaying the cells for a cellular marker, wherein detection of such a marker indicates increased likelihood of the presence of squamous cell carcinoma. Preferably said sampling is not directed to a particular site within the oesophagus. Preferably only the surface of the oesophagus is sampled. This has the advantage of avoiding more invasive sampling techniques such as biopsy collection techniques which penetrate below the surface of the oesophagus.

In another aspect, the invention relates to a non-invasive method for aiding the diagnosis of squamous cell carcinoma, comprising assaying cells from the surface of a subject's oesophagus for a cellular marker, wherein detection of such a marker indicates increased likelihood of the presence of squamous cell carcinoma. In this embodiment, preferably the actual sampling of the cells is not part of the method of the invention.

Preferably the method of the invention is conducted in vitro.

Preferably for Barrett's oesophagus or Barrett's associated dysplasia the marker is a non-squamous cellular marker.

Preferably the marker is a marker of cellular proliferation. This is particularly preferred for squamous cell carcinoma embodiments of the invention.

Preferably the marker is a marker of columnar cells.

In another aspect, the invention provides a method as described above wherein sampling the cellular surface of the oesophagus comprises the steps of (i) introducing a swallowable device as described above into the subject, (ii) retrieving said device by withdrawal through the esophagus, and (iii) collecting the cells from the device.

Preferably step (i) comprises introducing a swallowable device as described above into the subject's stomach.

Kits

In another aspect, the invention provides a kit comprising a device as described above. Suitably said kit further comprises a local anaesthetic. Preferably said local anaesthetic is a spray or lozenge, preferably a spray.

In another aspect, the invention provides a kit as described above further comprising a container for receiving said swallowable device after withdrawal, said container having a quantity of preservative fluid therein. Preferably the container is a watertight container. Preferably the preservative fluid is a cell preparation fluid. Preferably said fluid is thin preparation fluid for production of slides for examination of the sampled cells.

In another aspect, the invention provides a kit as described above wherein said device comprises a capsule sponge.

In another aspect, the invention provides a kit as described above wherein said swallowable device comprises withdrawal means such as string or cord.

In another aspect, the invention provides a kit as described above further comprising a device for severing said withdrawal means. Preferably said device comprises a blade or scissors.

In another aspect, the invention provides a kit as described above further comprising a container for administering drinkable fluid, such as water, to the subject.

In another aspect, the invention provides a kit as described above further comprising gloves. These advantageously protect the sample from contamination upon withdrawal of the device.

Preferably said kit further comprises reagent for use in the detection of a cellular marker.

In another aspect, the invention provides a kit as described above further comprising reagents for use in the detection of at least one marker selected from the group consisting of markers presented in Table 1, or the group consisting of markers presented in Table 2, or the group consisting of markers presented in Table 3.

In another aspect, the invention provides a kit further comprising a watertight container and preservative fluid. Preferably said fluid is for liquid based cytology, preferably said fluid is commercially available thin preparation fluid for production of slides for examination of the sampled cells.

In another aspect, the invention provides a kit as described above further comprising a local anaesthetic spray or lozenge.

In another aspect, the invention provides use of a device as described above in the diagnosis of Barrett's oesophagus or Barrett's associated dysplasia.

Barrett's Oesophagus and Dysplasia

Barrett's oesophagus can occur without dysplasia. Approximately 1% of patients with Barrett's oesophagus will develop dysplasia each year. At any given time, approximately 20% of patients with Barrett's oesophagus will have dysplasia. Cancer such as adenocarcinoma develops from dysplasia and is regarded as one extreme form of dysplasia, even though pathologically the conditions clearly differ. Adenocarcinoma is regarded as one extreme form of dysplasia, and its detection and diagnosis is discussed herein.

Thus it can be appreciated that the invention may be applied to detection and diagnosis of a single progressive disease state that has recognisable discrete stages. These stages comprise Barrett's oesophagus, Barrett's oesophagus associated dysplasia including adenocarcinoma, which arises therefrom.

The normal state of the cells in the oesophagus is that of squamous epithelium. In Barrett's oesophagus, these cells take on the characterisics of columnar epithelium and undergo further changes as they progress through the disease states outlined above. Thus, non-squamous cells in the oesophagus are abnormal and correlate with Barrett's oesophagus and potentially with dysplasia and more serious abnormalities as discussed herein.

Surface Sampling and Techniques

The device described facilitates sampling of the cells from the surface of the oesophagus using a swallowable abrasive material, which material is retrieved from the patient and from which the cells are subsequently separated for analysis.

Preferably substantially the entire surface of the oesophagus is sampled, preferably the entire surface e.g. the complete inner lumen.

By abrasive is meant that the material is capable of removing cells from the internal surface of the oesophagus. Clearly, since this is meant for use in a subject's oesophagus, 'abrasive' must be interpreted in the light of the application. Optimally the abrasive material needs to be abrasive enough to collect as many cells as possible, without causing damage to a subject's oesophageal lining. In the context of the present invention the term 'abrasive' has the meaning given above, which can be tested by passing the material through the oesophagus in an appropriate amount/configuration and examining it to determine whether cells have been removed from the oesophagus.

The material must be sufficiently abrasive to sample any dysplastic cells present in the oesophagus. Preferably the material is sufficiently abrasive to sample any Barrett's or adenocarcinoma cells present. In a most preferred embodiment, preferably the material is sufficiently abrasive to be capable of sampling the whole oesophagus ie. so that some squamous cells are collected together with any Barrett's and/or columnar and/or adenocarcinoma cells which may be present. This is advantageous because squamous cells are more difficult to remove than dysplastic cells and so their sampling provides a control to the operator such that if normal squamous cells are removed by the material then the chances of having not sampled the cells of interest such as Barrett's or dysplastic cells (if present), which are easier to remove than normal squamous cells, is correspondingly small.

Preferably the swallowable abrasive material is expandable. In this embodiment, preferably the abrasive material is of a smaller size when swallowed than when withdrawn. An expandable material may be simply a resilient material compressed such that when released from compression it will expand again back to a size approximating its uncompressed size. Alternatively it may be a material which expands eg. upon taking up aqueous fluid to a final size exceeding its original size.

In other words, preferably the material of the device expands, swells, inflates or otherwise increases in size between swallowing and withdrawal. Preferably the device is auto-expandable ie. does not require further intervention between swallowing and expansion. Preferably the device is not inflatable. Preferably the device expands by unfolding, unfurling, uncoiling or otherwise growing in size following removal of restraint after swallowing. Preferably the material of the device is compressible and reverts a size approximating its uncompressed size following swallowing. Preferably the device is constructed from a compressed material which is releasably restrained in a compressed state. Preferably the material is released from restraint after swallowing, allowing expansion of the device/material before withdrawal.

Preferably the device comprises compressible material which is compressed into capsule form. Preferably the compressible material is in the form of sponge material. Preferably the compressed sponge is at least partially surrounded by a soluble and/or digestible coat such as a capsule coat. Preferably the sponge is indigestible. Preferably the sponge comprises polyurethane such as polyurethane sponge, preferably reticulated polyurethane.

Preferably the capsule coat is at least partially formed from gelatine. Preferably the capsule coat is fully formed from gelatine.

In one embodiment it may be desirable to make the whole device out of digestible material to increase safety in case of a device becoming lost in the subject. Naturally the abrasive material would need to be digested at a slower rate than the capsule and the cord would need to be similarly slowly digested. Preferably the abrasive material is non-digestible. Preferably the cord is non-digestible.

Preferably the device is a capsule sponge. As will be apparent from the specification, a capsule sponge is a device comprising compressible sponge as the abrasive material, which sponge is compressed into a capsule shape, which capsule shaped compressed sponge is preferably reversibly restrained in its compressed state by at least a partial coat of soluble and/or digestible material such as gelatine.

Preferably the expanded (eg. decompressed) abrasive material of the device is approximately 3 cm in the plane perpendicular to the axis of the oesophagus.

Preferably this is the approximate diameter of the oesophageal lumen. More preferably this is slightly larger than the diameter of the oesophageal lumen, advantageously ensuring good contact with the inner surface of same as withdrawal/sampling takes place.

It is a feature of the invention that the sampling is not directed eg. visually directed to any particular part of the oesophagus. Preferably at least 10% of the oesophageal surface is sampled, preferably at least 20%, preferably at least 30%, preferably at least 40%, preferably at least 50%, preferably at least 60%, preferably at least 70%, preferably at least 80%, preferably at least 90%. In a most preferred embodiment, preferably substantially the entire oesophagus is sampled, preferably the whole inner lumen of the oesophagus is sampled. This applies equally to the in vitro sample even when the method of the invention does not include collection of the sample.

Screening and Surveillance

Screening aspects of the invention relate to the detection and/or diagnosis of Barrett's oesophagus. Typically in screening embodiments of the invention, the subjects being examined, or from which the sample(s) are (or were) obtained, are of unknown status for Barrett's.

Surveillance aspects of the invention relate to the detection and/or diagnosis of dysplasia, including adenocarcinoma. Although clearly dysplasia and adenocarcinoma are pathologically different conditions, adenocarcinoma can be regarded as one extreme form of dysplasia. As is discussed below, the invention may be advantageously applied to distinguish adenocarcinoma from dysplasia, depending upon the molecular markers used. However, in general the discussion of surveillance aspects of the invention relates to the detection of dysplasia, including adenocarcinoma. Typically in surveillance embodiments of the invention, the subjects being examined, or from which the sample(s) are obtained, are of unknown status for dysplasia but will typically be known to have Barrett's.

In principle the difference between screening and surveillance aspects is of little practical consequence to the working of the invention. The difference relates only to the markers chosen. The sampling and combination aspects remain the same between screening and surveillance. Indeed, it may be advantageous to combine screening and surveillance ie. to examine cell samples for markers of Barrett's as well as dysplasia including adenocarcinoma at the same time, thereby increasing the value of the information obtained and achieving a more robust combined diagnostic output.

Markers

Markers that can be applied for Barrett's screening and surveillance are any markers which are not expressed in normal oesophageal tissue, preferably any markers which ar not expressed in normal oesophagal surface cells.

Markers may be detected via nucleic acid based techniques (e.g. detection of expression by RNA detection) or by protein based techniques (e.g. immunochemistry using one or more antibodies recognising the polypeptide of interest; antibodies may be easily raised against a marker gene of interest for example by making recombinant protein and immunising a suitable host such as a rabbit or mouse). Some markers such as Alcian blue are in fact vital dyes (histochemical stains) and so are simply assayed directly.

For screening aspects (ie. for detection of Barrett's oesophagus), preferably markers that distinguish between intestinal metaplasia (Barrett's) and squamous oesophageal cells or gastric cardia are used. These markers include markers of epithelial differentiation.

The use of columnar markers is particularly preferred. The technical benefit of using columnar markers is that only columnar cells are detected by using them. This means that squamous cells (whether normal or cancerous) are not stained by columnar markers. This is an advantage because Barrett's cells and dysplastic cells arising therefrom such as adenocarcinoma cells are columnar and can thus be selectively identified by use of columnar marker(s). This advantageously improves signal and also reduces background and alleviates the need to apply further distinguishing markers, thereby simplifying the procedure by directly detecting columnar cells in this manner.

Any other markers known to be differentially expressed in Barrett's versus normal oesophageal surface cells may be employed.

Alternative markers may be identified using an expression microarray comparing gastric cardia and squamous cell biopsies. Any marker which is differentially present in these cell types may be used in the present invention.

For surveillance aspects, preferably markers whose expression correlates with the degree of dysplasia are used. Preferably such markers are used for the stratification of patients at risk. Preferably such markers include proliferation markers such as Ki67 and Mcm proteins, proliferation and DNA damage markers such as PCNA, cyclins such as cyclin D and/or cyclin A, aberrant p53 for example p53 LOH, p53 mutation, or p53 overexpression such as immunohistochemical detection thereof, p16 loss including methylation, and aneuploidy for example measured by flow cytometry or image cytometry. In slightly more detail, growth factors (such as EGF), growth factor receptors (such as EGFR) as well as cytokines (IL-4) and molecules involved in inflammatory response (COX-2) were shown to have an aberrant expression in BE and subsequent progression to AC, and are therefore useful markers according to the present invention. In vitro and ex vivo work has shown that acid and bile stimulation induced DNA damage, MAP kinase pathway and the NFκB pathway and decreased apoptosis therefore markers involved in the detection of DNA mutation and damage (e.g. ATM, ATR), markers of apoptosis (p53) and markers from the MAPK pathway (erk, p38) and markers from the NFκB are useful. Furthermore, bile acids increase the retinoic acid pathway (CYP26A1, RAR) which is linked to the induction of metaplasia in chick embryo oesophagus. A number of other pathways have been involved in the development of BE and progression to cancer such as TGFβ and BMP pathways.

Indeed, any marker known to correlate with the degree of dysplasia would be suitable, including many oncogenes and tumour suppressor genes. In particular, markers mentioned in Fitzgerald R C Clin Gastroenterol Hepatol Complex diseases in gastroenterology and hepatology: GERD, Barrett's, and esophageal adenocarcinoma. 2005, 3:529-37 or in Fitzgerald RC Recent Results in Cancer Res Genetics and prevention of oesophageal adenocarcinoma 2005, 166:35-46 may be suitable for use in the present invention.

Most suitable markers according to the present invention are now discussed.

We describe genes with potential as biomarkers for use in the invention for example in analysing cells harvested with capsule sponge.

Thus we disclose biomarkers for detection of Barrett's oesophagus. The following table gives a breakdown of the number of genes at each stage of the experimental process. The further in the process the better marker a particular gene is likely to be.

| Process/Type | Public dataset | In house dataset |
| --- | --- | --- |
| Dysregulated genes | 18 | 191 |
| Taken to PCR | 18 | 20 |
| Validated by PCR | 3 | 9 |
| Taken to immunohistochemistry | 3 | Ongoing |
| Validated by immunohistochemistry | 2 | N/A |
| Genes taken to capsule sponge | 2 | N/A |

The 20 genes from the in house datasets taken to the PCR were selected according to:
High level of expression and high statistical significance
Presence of suitable antibodies
Specific markers are now discussed in more detail:

TABLE 1

3 markers currently used with capsule sponge

| Marker (e.g. gene) name | Details e.g. Gene bank accession number(s) | Notes |
| --- | --- | --- |
| Alcian blue | Not a gene target but an histochemical staining technique | |
| Mcm2 | NM_004526 | Mcm 2 may be used for squamous cell carcinoma |
| TFF3 | NM_003226 | |

TABLE 2

11 Markers validated at the PCR level.
(Validation at the protein level may be carried out if desired.)

| Marker name | Details e.g. Gene bank accession number(s) | |
| --- | --- | --- |
| ABP1 | NM_001091 | |
| DDC | NM_000790 | NM_001082971 |
| HOX C10 | NM_017409 | |
| KCNE3 | NM_005472 | |
| LAMC2 | NM_005562 | NM_018891 |
| MUC13 | NM_033049 | |
| MUC17 | NM_001040105 | |
| NMUR2 | NM_020167 | |
| PIGR | NM_002644 | |
| TSPAN1 | NM_005727 | |
| HOXB5 | NM_002147 | |

TABLE 3

161 Genes differentially expressed between Barrett's vs normal oesophagus and gastric cardia. The genes are ordered from the most advantageous to the least preferred (highest statistical significance and expression level to lowest significance and expression level).

| GeneSymbol | Gene bank accession number(s) | | | |
| --- | --- | --- | --- | --- |
| RNF217 | NM_152553 | | | |
| CCL28 | NM_148672 | | | |
| AGR3 | NM_176813 | | | |
| CFTR | NM_000492 | | | |
| PAQR5 | NM_001104554 | NM_017705 | | |
| BNIP3 | NM_004052 | | | |
| GOLM1 | NM_177937 | | | |
| PLA2G10 | NM_003561 | | | |
| KCNK5 | NM_003740 | | | |
| MLSTD1 | NM_018099 | | | |
| SLC16A7 | NM_004731 | | | |
| NFE2L2 | NM_006164 | | | |
| CGNL1 | NM_032866 | | | |
| CALML4 | NM_001031733 | NM_033429 | | |
| ACSL5 | NM_016234 | NM_203380 | NM_203379 | |
| KRT8 | NM_002273 | | | |
| TMC7 | NM_024847 | | | |
| FAT | NM_005245 | | | |
| CES3 | NM_024922 | | | |
| SLC7A7 | NM_003982 | | | |
| REG4 | NM_032044 | | | |
| CATSPERB | NM_024764 | | | |
| TSPAN3 | NM_005724 | NM_198902 | | |
| SLC37A1 | NM_018964 | | | |
| GPRC5A | NM_003979 | | | |
| GPT2 | NM_133443 | | | |
| PAIP2B | NM_020459 | | | |
| TRIM29 | NM_012101 | | | |
| IL18 | NM_001562 | | | |
| HSD17B11 | NM_016245 | | | |
| GSDML | NM_001042471 | NM_018530 | | |
| TACSTD1 | NM_002354 | | | |
| HSD17B2 | NM_002153 | | | |
| KRT7 | NM_005556 | | | |
| CLIC6 | NM_053277 | | | |
| ATP2C2 | NM_014861 | | | |
| HEPH | NM_014799 | NM_138737 | | |
| TPD52L1 | NM_003287 | NM_001003395 | NM_001003396 | NM_001003397 |
| HOXB6 | NM_018952 | | | |
| PLS1 | NM_002670 | | | |
| IL1RN | NM_173841 | NM_173842 | NM_173843 | NM_000577 |
| NT5E | NM_002526 | | | |
| CAB39L | NM_001079670 | NM_030925 | | |
| S100A14 | NM_020672 | | | |
| GDA | NM_004293 | | | |
| TRIM31 | NM_007028 | | | |
| ARPC1B | NM_005720 | | | |
| SLC16A1 | NM_003051 | | | |

TABLE 3-continued

161 Genes differentially expressed between Barrett's vs normal oesophagus and gastric cardia. The genes are ordered from the most advantageous to the least preferred (highest statistical significance and expression level to lowest significance and expression level).

| GeneSymbol | Gene bank accession number(s) | | | |
|---|---|---|---|---|
| TMC5 | NM_024780 | NM_001105248 | NM_001105249 | |
| CPEB2 | NM_182646 | NM_182485 | | |
| LOC93432 | ENST00000397504 | | | |
| F5 | NM_000130 | | | |
| VLDLR | NM_003383 | NM_001018056 | | |
| GCNT3 | NM_004751 | | | |
| MBOAT2 | NM_138799 | | | |
| CPS1 | NM_001875 | | | |
| GALM | NM_138801 | | | |
| DGKD | NM_152879 | NM_003648 | | |
| FAM102B | NM_001010883 | | | |
| LYN | NM_002350 | | | |
| SFN | NM_006142 | | | |
| GALNT7 | NM_017423 | | | |
| EMP1 | NM_001423 | | | |
| CSTB | NM_000100 | | | |
| RHOC/ | NM_001042678 | NM_175744 | NM_001042679 | |
| FLJ14959 | AK027865 | | | |
| SNRPN | NR_001294 | | | |
| ANKS4B | NM_145865 | | | |
| PCLKC | NM_017675 | | | |
| ADH7 | NM_000673 | | | |
| LYZ | NM_000239 | | | |
| S100A16 | NM_080388 | | | |
| SLC6A20 | NM_020208 | NM_022405 | | |
| SCNN1G | NM_001039 | | | |
| HKDC1 | NM_025130 | | | |
| SLC7A2 | NM_001008539 | NM_003046 | | |
| SPG20 | NM_015087 | | | |
| 37681 | NM_178450 | | | |
| FGFBP1 | NM_005130 | | | |
| CA9 | NM_001216 | | | |
| RDX | NM_002906 | | | |
| SAMD9 | NM_017654 | | | |
| SERPINB5 | NM_002639 | | | |
| NMU | NM_006681 | | | |
| CLRN3 | NM_152311 | | | |
| SLC9A4 | NM_001011552 | | | |
| VTCN1 | NM_024626 | | | |
| LOC339977 | NM_001024611 | | | |
| FUT9 | NM_006581 | | | |
| GALNT5 | NM_014568 | | | |
| NR5A2 | NM_205860 | NM_003822 | | |
| OLFM4 | NM_006418 | | | |
| LY75 | NM_002349 | | | |
| SCPEP1 | NM_021626 | | | |
| TACSTD2 | NM_002353 | | | |
| MYO1A | NM_005379 | | | |
| BTNL8 | NM_024850 | NM_001040462 | | |
| VIL1 | NM_007127 | | | |
| SLC28A2 | NM_004212 | | | |
| DPP4 | NM_001935 | | | |
| AZGP1 | NM_001185 | | | |
| CDH17 | NM_004063 | | | |
| NPNT | NM_001033047 | | | |
| ALDH1A1 | NM_000689 | | | |
| ATP13A4 | NM_032279 | | | |
| ATP7B | NM_000053 | NM_001005918 | | |
| IL2RG | NM_000206 | | | |
| POSTN | NM_006475 | | | |
| FCGBP | NM_003890 | | | |
| GPA33 | NM_005814 | | | |
| DSC2 | NM_024422 | NM_004949 | | |
| COL6A3 | NM_057167 | NM_057165 | NM_057164 | NM_004369 |
| VNN1 | NM_004666 | | | |
| SLPI | NM_003064 | | | |
| AIM1 | NM_001624 | | | |
| PRKAA2 | NM_006252 | | | |
| GUCY2C | NM_004963 | | | |
| PI3 | NM_002638 | | | |
| TIMP1 | NM_003254 | | | |
| APOL1 | NM_003661 | NM_145343 | | |
| ANPEP | NM_001150 | | | |

TABLE 3-continued

161 Genes differentially expressed between Barrett's vs normal oesophagus and gastric cardia. The genes are ordered from the most advantageous to the least preferred (highest statistical significance and expression level to lowest significance and expression level).

| GeneSymbol | Gene bank accession number(s) | | |
|---|---|---|---|
| SLC34A2 | NM_006424 | | |
| DMBT1 | NM_007329 | NM_004406 | NM_017579 |
| RGS2 | NM_002923 | | |
| PAPSS2 | NM_004670 | NM_001015880 | |
| BCMO1 | NM_017429 | | |
| ADH6 | NM_000672 | NM_001102470 | |
| TM4SF20 | NM_024795 | | |
| CHST5 | NM_024533 | | |
| HHLA2 | NM_007072 | | |
| FABP1 | NM_001443 | | |
| SNORD116-21 | NR_003335 | NR_003106 | |
| MYO7B | NM_001080527 | | |
| MIA | NM_006533 | | |
| MEP1A | NM_005588 | | |
| SLC3A1 | NM_000341 | | |
| PLAC8 | NM_016619 | | |
| TFPI | NM_006287 | NM_001032281 | |
| PGC | NM_002630 | | |
| MUC2 | ENST00000361558 | | |
| LIPF | NM_004190 | | |
| FABP2 | NM_000134 | | |
| SI | NM_001041 | | |
| SLC17A4 | NM_005495 | | |
| GSTA1 | NM_145740 | | |
| PDZK1 | NM_002614 | | |
| RAB3B | NM_002867 | | |
| REG1A | NM_002909 | | |
| SPINK4 | NM_014471 | | |
| CXCL1 | NM_001511 | | |
| GKN1 | NM_019617 | | |
| BTNL3 | NM_197975 | | |
| ADH4 | NM_000670 | | |
| ALDOB | NM_000035 | | |
| CXCL2 | NM_002089 | | |
| SLC26A3 | NM_000111 | | |
| MMP7 | NM_002423 | | |
| UPK1B | NM_006952 | | |
| MEP1B | NM_005925 | | |
| CA1 | NM_001738 | | |
| PRSS7 | NM_002772 | | |

Most suitably all markers shown above may be used (e.g. 161 from table 3; plus 11 from table 2; plus 3 from table 1). This has the advantage of maximising statistical significance and eliminating any potential artefacts in the results. However, assessing this quantity of markers may become impractical or indeed unnecessary for many applications. Thus, suitably up to 11 markers are assayed.

Clearly the number of markers assayed will depend on the format or mode chosen by the operator for analysis. In a primary care setting the emphasis may be on simplicity and/or avoidance of use of specialist equipment and so the number of markers may be minimised in such settings, for example to three or fewer markers of Table 1.

When an array such as a nucleic acid array is used to analyse the markers, it is very straightforward to analyse multiple markers on a single array or chip. Thus for these modes of analysis, greater numbers of markers may be used such as 50, 100, 150, 161 or even more.

Multiplex PCR may be used to assay the markers. In this embodiment suitably up to 20 markers may be analysed in the same procedure.

Most suitably markers used are one or more of those shown in table 1; more suitably two or more of those shown in table 1; most suitably each of those shown in table 1.

Most suitably Trefoil factor 3 (TFF3) is a marker used in the present invention. TFF3 and its use is described in WO2005/013802.

Marker Assay/Detection

Assaying for a marker means determining the presence or absence of said marker. Preferably assaying means immunological staining or visualisation of the marker.

Marker expression (marker gene expression) may be detected by any suitable means known to those skilled in the art. Expression may be detected at the nucleic acid or protein level. Expression may be by mass spectrometry and assignment of the mass readouts to particular protein moieties. At the nucleic acid level, detection is preferably by monitoring of mRNA levels. Preferably expression is detected at the protein level. Preferably marker gene expression refers to marker protein expression. Preferably marker protein expression is determined by direct or indirect detection of marker protein. Preferably such protein is detected by immunochemical means.

Preferably the marker protein is detected by an antibody capable of reacting with that protein, and subsequent visualisation of said antibody. Preferably the antibody is a polyclonal antibody or a monoclonal antibody. Preferably when the antibody is a polyclonal antibody it is an immunopurified polyclonal antibody. Preferably the antibody is a monoclonal antibody. Use of secondary and even tertiary or further antibodies may advantageously be employed in order to amplify the signal and facilitate detection. Preferably marker protein(s) are visualised by use of immunohistochemical means, such as immunofluorescent means, directly or indirectly bound to the marker protein(s). Preferably detection is by antibody to the marker.

Other suitable assays include ELISA—fluorescent in-situ hybridisation of fish and FACS—fluorescence analysis of cell sorting.

Sample

It will be appreciated that the sample preferably comprises a population of individual cells obtained by the sampling procedures described herein. Thus, the detection of the markers preferably refers to detection of the markers in at least one cell within said population of cells. The detection of an appropriate marker in any cells in the sample will be indicative of Barrett's or a Barrett's associated dysplasia. The absence of any cells showing the marker from the population of cells of the sample will be indicative of lack of Barrett's or Barrett's associated dysplasia. The proportion of cells showing expression of the marker is less important. The proportion of cells showing expression of the marker would not usually make a contribution to the diagnosis. The present invention is based on the detection of any cell(s) showing the marker in the sampled cell population, or the apparent absence of any cells showing the marker. In some embodiments, it may be advantageous to determine the relative proportions of the cell types or the proportion of cells displaying proliferative markers, as an optional step dependent on the needs of the operator. However, for most embodiments of the invention, the result will be expressed as a positive or negative, and the relative proportions of cells will normally not be taken into consideration.

Kits

The kits of the invention are designed to provide for conducting the methods of the present invention. Thus, the description of elements required for the methods of the invention applies equally to the contents of the kits of the invention, which preferably contain the elements required for practice of said methods. In particular, preferably the kits contain reagent for detection of the marker or markers being used.

Preferably the kit of the invention also contains a local anaesthetic for use in the oesophagus. Preferably this may be in the form of a spray or lozenge, preferably a spray.

Preferably the kit of the invention also contains a container for holding the device once withdrawn from the subject. Preferably this container is watertight. Preferably the container contains a preservative fluid. Preferably the container contains a liquid based cytology fluid such as commercial thin preparation fluid for producing slides of the sampled cells. Preferably the thin preparation fluid comprises a preservative.

Preferably the swallowable device is lubricated to aid swallowing, preferably the withdrawal means is also lubricated. Thus, preferably the kit comprises lubricant.

Preferably the kit comprises a drinkable solution to aid swallowing the device. Preferably said solution is flavoured to disguise the taste of the device, or to render it more palatable. Preferably said solution is thickened eg. by addition of sugar or pectin or other agent giving rheological characteristics such as viscosity or thickness. The advantage of this is that a more viscous or dense solution will be more effective at aiding passage of the device through the oesophagus during swallowing.

In order to save weight/volume in kits, preferably the solution(s) supplied are supplied in powdered form such that the operator reconstitutes them before use eg. by adding water. Preferably the kit comprises a container for reconstitution. Preferably said container is graduated to facilitate measurement of the correct amount of fluid such as water.

Preferably the swallowable device does not comprise animal product(s).

Preferably the kit comprises anti-emetic eg. in lozenge, solution or powdered form, to suppress any urge to vomit during introduction and/or withdrawal of the device.

Preferably the kit may comprise antacid such as acid-neutralising compound(s), or such as pharmaceutical antacid for inhibition of acid production/secretion in the stomach. Advantageously this may be used to inhibit a burning sensation of acid carried up the oesophagus from the stomach upon withdrawal of the device. Furthermore, this may be advantageous in preservation of the cell samples obtained with said device.

Preferably the preservative fluid contains antacid and/or is buffered to the desired pH for preservation of the cell sample obtained.

In one embodiment the kit preferably comprises a local anaesthetic spray, a capsule sponge, a pot containing prep liquid (e.g. ThinPrep™ PreservCyt™ Solution™), a label for the pot, and an instruction leaflet for a health care professional who administers the sampling.

Preferably the kit further comprises gloves (for health care professional such as a nurse removing the capsule from the subject).

Preferably the kit further comprises scissors to cut the withdrawal means (e.g. cord).

Preferably the kit further comprises a plastic cup (for subject to drink fluid e.g. water).

Preferably the kit further comprises an information leaflet for the subject/patient.

In another embodiment the invention relates to a self testing kit such as a dip-stick format kit whereby said stick comprises reagents for detection of markers according to the present invention and wherein in use dipping the stick into the pool of sampled cell material leads to a visualised readout of the markers according to the present invention, thereby providing information capable of aiding diagnosis as set out herein.

The device comprises withdrawal means. Preferably this is a string or cord based means. Preferably the withdrawal means is graduated so that the operator can estimate when the device is, or is likely to be, in the stomach. Furthermore, the graduations advantageously allow monitoring of withdrawal of the device and allow for standardisation of the rate of withdrawal and for optimisation of sample collection.

Preferably the withdrawal means comprises an unswallowable element at the end distal from the swallowable abrasive material. This advantageously prevents accidental swallowing of the entire device, inhibiting or preventing its withdrawal. Preferably this unswallowable element is detachable in case of emergency when it may be safer to allow the entire device to be swallowed and passed through the alimentary canal.

Further Kit Features

In some embodiments, it is probable that there will be a multi-part kit to provide for different elements in different settings. The discussion above is focussed on the preferred aspects of the kit of the invention which is the primary care application e.g. in screening for intial detection in a subject. However, it will be apparent to the skilled person that the oesophagus surface sample may be analysed at a location different from the initial primary care setting in which subject(s) are sampled. For example, the cell(s) may be analysed in a laboratory separate from the primary care setting in which the sample is collected. In this embodiment it is apparent that the invention may relate to multi-part kit(s) having a primary care component as well as a read-out component (or laboratory component), or the invention may even relate to the read-out/laboratory component of the kit per se. In this example, the read-out (or laboratory) component of the kit may comprise one or more of the following elements:

Consumables such as non-gynaecological microscope slides, and/or non-gynaecological filters.

Equipment such as ThinPrep™ 2000 processor.

Detection of abnormal pathology—for the detection of Barrett's oesophagus using immunohistochemistry; System for automated immunostaining e.g. if the samples are stained using the DakoCyomation Ltd ChemMate™ system.

The kit may further comprise one or more of the following detection consumables such as Dako Autostainer reagents vial; ChemMate™ detection kit; ChemMate™ Peroxidase blocking solution; ChemMate™ antibody diluent; Mcm2 antibody; Goat serum; Bovine serum albumin; Haematoxylin and/or Coverslips.

The kit may further comprise equipment such as Dako autostainer slides processor (S3400 Dako autostainer).

In order to facilitate analysis of the samples, the kit may comprise visualisation means such as a microscope (such as an automated microscope) e.g. Olympus BX41 with X10, X20 and/or X40 objectives.

Further Advantages/Applications

Once tissue architecture is lost as in surface sampling, cytologists can no longer tell cell types such as squamous, columnar, Barrett's etc apart. Furthermore, observation of inflammatory cells such as lymphocytes no longer contributes to the diagnosis since no positional information can be gleaned from their observation. However, advantageously the present invention overcomes this problem by employing biomarkers to identify the cell types even when the histological information has been lost.

Although it is preferred to assay the cells by distribution onto slides, it may be advantageous to perform the assay in a different format such as ELISA or FACS or FISH. Preferably the cells can be assayed in one or more of these format(s) directly from the capsule sponge or washings therefrom, advantageously avoiding the need for a slide format analysis. If a slide format analysis is required, preferably cells are concentrated onto the slides to produce fewer slides for the same number of cells, thereby saving costs. In one embodiment, preferably the cells from the capsule sponge are collected and their protein extracted and tested for the marker(s), thereby alleviating the need for whole cell staining.

Advantageously pore size on the preferred capsule sponge sampling device can be varied to regulate the number of cells harvested. For example, by reducing pore size the number of cells (and thus the number of slides needed) may be advantageously reduced. In highly preferred embodiments, markers are chosen to detect high risk Barrett's. This has the further advantage that surveillance ie. remonitoring of patients with Barrett's to detect future dysplasia including adenocarcinoma may be reduced or rendered unnecessary since in one step the Barrett's is detected and graded as high risk, so subsequent treatment can be prescribed immediately without expensive surveillance, and without the risk that during surveillance the patient will go on to develop more dangerous lesions before detection.

It is an advantage of the present invention that false negatives are extremely rare. Some false positives can occur, eg. detection of naturally proliferating cells such as closing a wound incurred by swallowing an abrasive foodstuff such as a fruit stone. However, a negative result from the tests and kits of the present invention is very reliable so that patients can be excluded from unnecessary follow up procedures and can receive robust reassurance at an early stage when a negative result is obtained.

Since the methods and kits of the invention are simple and low in cost, a much wider screening programme can be undertaken for the same net cost to the service provider.

Preferably the tests of the present invention are carried out on a given subject at 3 year intervals.

Another advantage of the invention is that the first signs of dysplasia can be very small and may be missed by visual inspection or endoscopic biopsy sampling, but will be detected according to the present invention. Similarly, 40% of subjects with high grade dysplasia already have the cancer present. The present invention advantageously allows better detection/diagnosis of these patients.

Use of sponge material as the abrasive material has the advantage of being able to collect cells throughout its structure due to its preferred mesh construction, rather than being limited to collection on the cell surface. This has the advantage of increased yields.

Further Applications

Suitably the device of the invention may be applied for sampling of squamous cells such as in aiding the diagnosis or prognosis of squamous carcinoma. This application may be as well as, or as a separate application from, sampling of oesophageal cells such as Barrett's oesophageal cells for aiding the diagnosis or prognosis of Barrett's oesophagus, dysplasia, or adenocarcinoma.

Thus the device described herein finds application in squamous cell carcinoma—suitably the biomarkers used will be chosen accordingly in this application of the invention. For aiding the diagnosis or prognosis of squamous carcinoma, suitably the markers used are markers of cellular proliferation. For squamous carcinoma applications, Mcm2 is a most suitable biomarker.

The present invention will now be described, by way of example only, in which reference will be made to the following figures:

EXAMPLES

Example 1

Construction of Device

Figure 1:
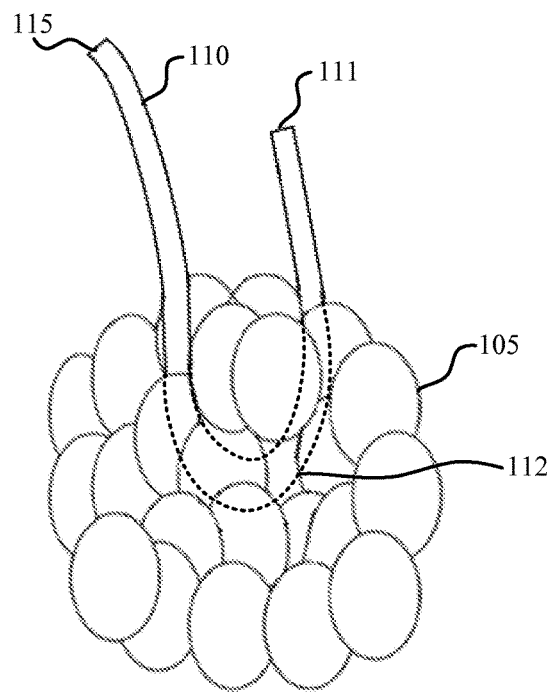
FIG. 1 shows an exemplary construction of a cell sampling device with a cord under a surface of an abrasive material sponge in accordance with various embodiments.

An exemplary device has the following features or components
- abrasive material: Sponge 105 (composition: reticulated polyurethane; density: 10 ppi; shape: spherical; diameter: 3 cm; supplier: Foam Conversion Ltd, Kempston, Bedforshire, UK)
- means for retrieval: Cord 110 (reference: White Force Fiber Code F500-W; size: No 2; supplier: Teleflex Medical, USA)
- soluble capsule 125 (reference: Gelatin Capsule; size: 00; supplier: Capsuline Inc., USA)
- unswallowable element 130: Cardboard retaining the loose end of the cord 110 (supplier: Medical Wire & Equipment Ltd, UK)

The device is optionally packaged:
Packaging (composition: sealed polythene bag; supplier: Medical Wire & Equipment Ltd, UK)

The device may be irradiated with a minimum dose of 17 kGy, which is at a level necessary to clean the device but not sterilise it. The device may be optionally irradiated with a sterilizing dose of radiation.

The knot 120 used in tying the thread 110 through and out of the capsule sponge 105:

Free end of 111 the thread 110 is passed in to the open sponge 105 in such a way that the thread 110 forms a small loop 112 with in the sponge 105 just below the surface as shown in the FIG. 1.

The free end 111 of the thread 110 is brought out and a loop is made using two overhand knots 113, 114 (noose) one after the other (double overhand knot 120).

Note that it is basically two overhand knots 1134, 114, with the second overhand knot 113 acting as a stop-knot.

Figure 2:
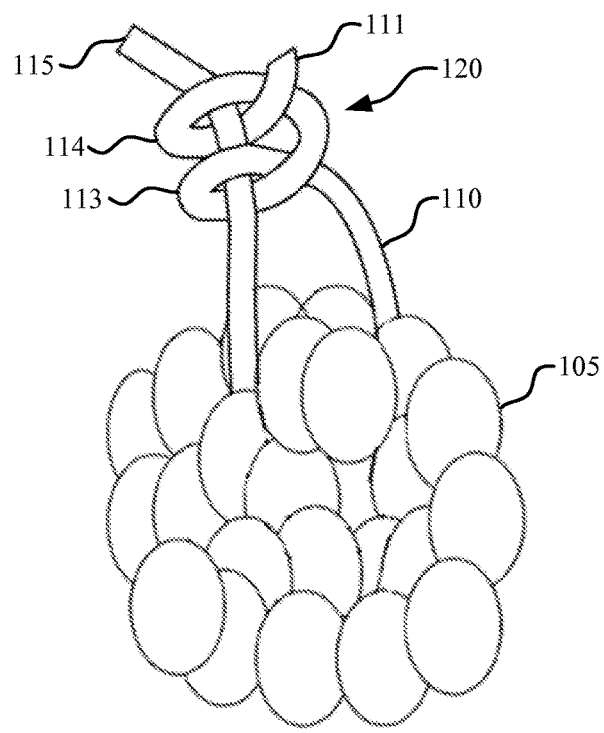
FIG. 2 shows an exemplary construction of a cell sampling device with a cord under a surface of an abrasive material sponge in accordance with various embodiments.

The other free end 115 of the thread 110 is passed through this loop and pulled tight as in FIG. 2.

At least 1 cm length is left at the free end 111 of thread 110 after the knot 120.

The cord 110 runs under the surface of the sponge 105. The cord 110 may optionally run through deep in the centre of the sponge 105 sphere.

The short loose end 111 of the cord 110 is at least 1-centimeter-long.

Figure 3:
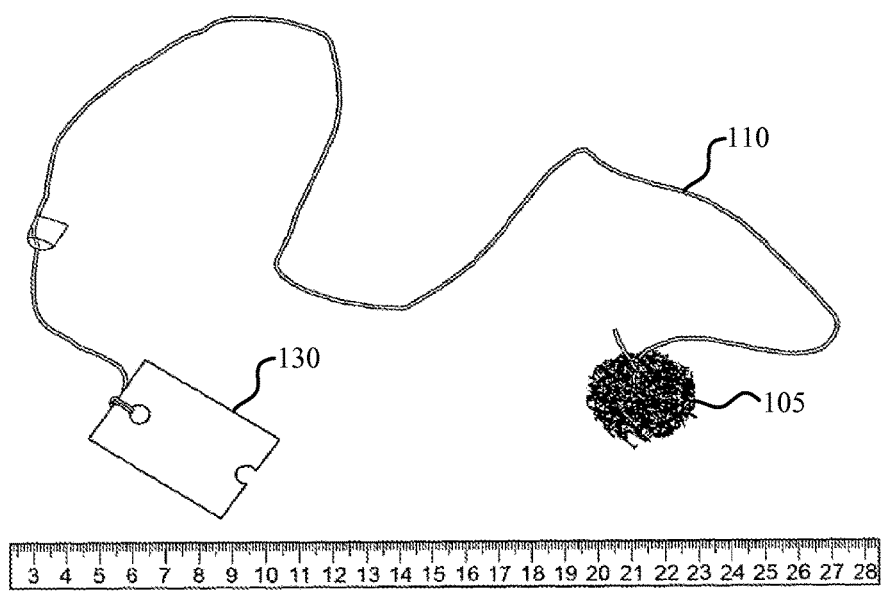
FIG. 3 shows an illustration of an exemplary cell sampling device of the invention in accordance with various embodiments.

The long loose end 115 of the cord 110 shall be wound round and attached to an unswallowable element 130 which comprises a flat piece of cardboard (5-centimeter-long and 3-centimeter-wide) as shown in FIG. 3.

80 centimeters of cord 110 shall be allowed for each sponge kit, including the knot 120.

Figure 4:
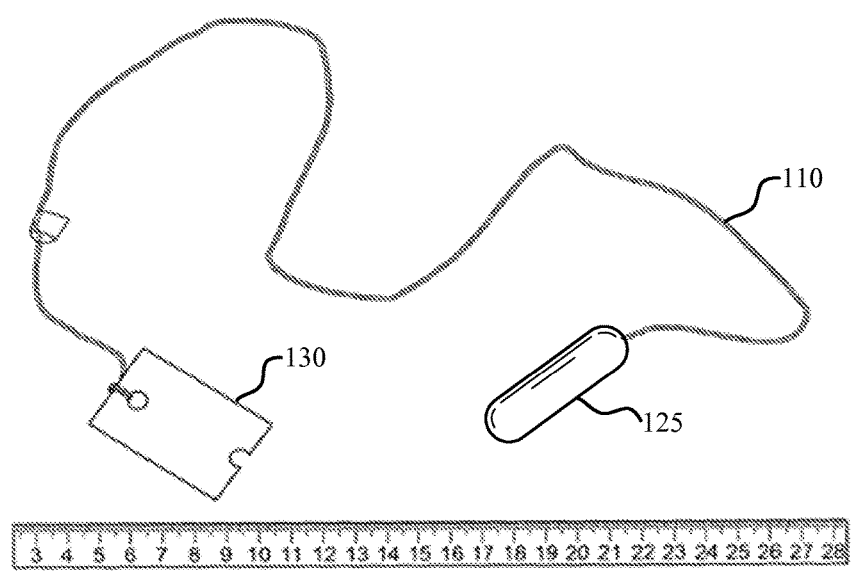
FIG. 4 shows an illustration of an exemplary cell sampling device of the invention in accordance with various embodiments.

The assembled device is then encapsulated into the soluble capsule 125 as shown in FIG. 4.

Example 2

Further Properties and Features

Devices of the invention may be tested to check their performance and properties.

Devices may be tested as follows:
- measure the length of the cord from the end to the outer surface of the capsule—it should be 60 centimeters minimum
- look for any breaks on the outside of the capsule—any breaks should be remedied
- calculate the time taken for the capsule to dissolve and the sponge to open in warm water at 30 degree C.—it should be 5 minutes maximum
- measure the size of the loop inside the sponge
- check the loop—should be just below the surface of the sponge
- measure the free end of the cord after the knot—it should be 1 centimeter in length minimum
- check that the knot complies with specifications set out herein
- measure the diameter of the sponge once the capsule dissolved after 5 minutes—it should be 3 centimeters
- measure the weight the cord can hold before either tearing the sponge apart or the thread getting undone from the sponge—the cord should hold 2.4 kg minimum

Example 3

Comparative Data

Devices according to the present invention were tested as above. Known (old) devices were tested in parallel to demonstrate the technical advantages of the device of the invention.

Exemplary features of a device according to the present invention include the following:
Sponge:
Shape—round
Diameter—3cm
Capsule:
Uniform shape and size
Not have any breaks and sharp ends
Dissolves in 30 degree centigrade water within 5 minutes
Retrieval means:
Cord
White colour thread
Minimum length of cord—60 cms
Smooth on the surface
Loop inside the sponge—should loop just below the surface
Free end of the cord after the knot—minimum of 1 cm
Knot—Double hitch knot and complies with the specifications given
Break resistant—Minimum requirement of 2.4 kg
Cord tethered to unswallowable element such as cardboard to prevent swallowing
Test performance of the known sponge (old sponge) in vitro:

| No | Length of cord in cm | Capsule outside | Time taken to open in H20 at 30 C. | Loop inside the sponge | Free end of thread | Knot specification | Weight withstood | Fate when max. tension exceeded | Sponge size when opened |
|---|---|---|---|---|---|---|---|---|---|
| 1 | 77.5 | Larger size, Broken | 6 min 11 sec | Fine | 0.7 cm | Fine | 1.42 kg | Thread broke | 3 cm |

-continued

| No | Length of cord in cm | Capsule outside | Time taken to open in H20 at 30 C. | Loop inside the sponge | Free end of thread | Knot specification | Weight with-stood | Fate when max. tension exceeded | Sponge size when opened |
|---|---|---|---|---|---|---|---|---|---|
| 2 | 75.5 | Fine | 4 min 54 sec | Fine | 0.8 cm | Fine | 2.11 kg | Thread broke | 3 cm |
| 3 | 77 | Fine | 6 min 02 sec | Small | 0.8 cm | Fine | 3.10 kg | Thread broke | 2.8 cm |
| 4 | 77 | Fine | 6 min 29 sec | Fine | 0.8 cm | Fine | 2.51 kg | Thread broke | 2.5 cm |
| 5 | 77.5 | Fine | 4 min | Fine | 0.7 cm | Fine | 2.19 kg | Thread broke | 3 cm |
| 6 | 78 | Fine | 6 min 20 sec | Fine | 0.8 cm | Fine | 2.65 kg | Thread broke | 2.8 cm |
| 7 | 78.5 | Fine | 6 min 29 sec | Small | 0.9 cm | Fine | 2.41 kg | Thread broke | 2.5 cm |
| 8 | 77 | Fine | 5 min 49 sec | Fine | 0.8 cm | Fine | 2.43 kg | Thread broke | 3.1 cm |
| 9 | 76 | Fine | 3 min 02 sec | Fine | 2 cm | Fine | 2.38 kg | Thread broke | 2.8 cm |
| 10 | 78 | Fine | 4 min 32 sec | Fine | 2 cm | Fine | 2.41 kg | Thread broke | 2.8 cm |

Performance of the device of the invention (new sponge) in vitro:

| No | Length of cord in cm | Capsule outside | Time taken to open in H20 at 30 C. | Loop inside the sponge | Free end of thread | Knot specification | Weight with-stood | Fate when maximum tension exceeded | Sponge size when opened |
|---|---|---|---|---|---|---|---|---|---|
| 1 | 69 | Fine | 2 min 06 sec | Fine | 1 cm | Fine | 3.5 kg | Tore through the sponge | 3 cm |
| 2 | 67 | Fine | 2 min 09 sec | Fine | 1.5 cm | Fine | 5.8 kg | Same as above | 3 cm |
| 3 | 66 | Fine | 3 min 53 sec | Small | 1.5 cm | Fine | 4.06 kg | Same as above | 3 cm |
| 4 | 64 | Fine | 3 min 06 sec | Fine | 1.7 cm | Fine | 4.89 kg | Unable to break | 3 cm |
| 5 | 68 | Fine | 3 min | Fine | 1.7 cm | Fine | 5.7 kg | Unable to break or separate | 3 cm |
| 6 | 68 | Fine | 2 min 09 sec | Fine | 1.6 cm | Fine | 5.67 kg | Unable to break | 3 cm |
| 7 | 66 | Fine | 2 min 22 sec | Small | 2 cm | Fine | 4.35 kg | Tore through the sponge | 3 cm |
| 8 | 67 | Fine | 3 min 30 sec | Fine | 2 cm | Fine | 2.78 kg | Same as above | 3 cm |
| 9 | 66 | Fine | 3 min 02 sec | Fine | 2 cm | Fine | 5.9 kg | Same as above | 3 cm |
| 10 | 68 | Fine | 4 min 32 sec | Fine | 2 cm | Fine | 5.49 kg | Unable to break or separate from the sponge | 3 cm |

IN SUMMARY

Thus it can be seen that the old (known) device is inferior in several respects. The

| | Median length of chord in cm (Range) | Time taken to open in H20 at 30 C. | Capsule outside (Range) | Loop inside the sponge (Range) | Free end of thread | Knot specification | Weight withstood | Sponge size when fully open | Fate when max tension exceeded |
|---|---|---|---|---|---|---|---|---|---|
| Old Sponge Kit | 77 cm (75-78.5 cm) | 6.02 sec (4 to 6.29 sec) | Fine | Fine | 0.8 cm (0.7 to 0.9 cm) | Variable knots | 2.41 kg (1.42 kg to 3.10 kg) | 2.8 cm (2.5 to 3 cm) | Thread snapped in all 10 tests |
| New Sponge Kit | 67 cm (64 to 69 cm) | 3.01 min (2.06 to 4.32 min) | Fine | Fine | 1 cm | Two half hitch knot | 4.62 kg (2.78 to 5.8) | 3 cm | Majority - thread tore through the sponge | advantageous performance of the device of the invention can be clearly appreciated.

In addition it should be noted that in in vivo tests, there have been no losses of the device in subjects, as compared to the known old device which has regularly been lost in subjects.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A swallowable cell sampling device comprising:
   an abrasive and sponge-like material capable of collecting cells from a surface of a human esophagus;
   a means for retrieval comprising a cord;
   an attachment loop formed by looping the cord around a central portion of the abrasive material; and
   a hitch knot adjustably securing the attachment loop such that during retrieval of the cell sampling device, tightening of the attachment loop compresses the central portion of the abrasive material while an outer diameter of the abrasive material remains substantially constant.

2. The device according to claim 1, wherein the hitch knot is a double overhand knot.

3. The device according to claim 1, wherein the abrasive material is compressible.

4. The device according to claim 1, wherein the abrasive material comprises reticulated polyurethane.

5. The device according to claim 1, wherein the abrasive material is compressed and wherein the abrasive material is retained in a compressed state by a soluble capsule.

6. The device according to claim 5, wherein the soluble capsule comprises a gelatin capsule.

7. The device according to claim 6, wherein the capsule is capable of dissolution and the abrasive material is capable of reverting to its uncompressed size within 5 minutes upon immersion in water at 30 degrees Celsius.

8. The device according to claim 1, wherein the cell sampling device further comprises an unswallowable element coupled with the cord at an end distal from the abrasive material.

9. A kit comprising a device according to claim 1, and at least one reagent for use in detecting a cellular marker.

10. The kit according to claim 9, wherein the cellular marker is selected from the group consisting of Mcm2 and TFF3.

11. The kit according to claim 9, wherein the cellular marker is selected from the group consisting of ABP1, DCC, HOX C10, KCNE3, LAMC2m MUC13, MUC17, NMUR2, PICR, TCPAN1, and HOXB5.

12. The kit according to claim 9 wherein the cellular marker is selected from the group consisting of RNF2I7, CCL28, AGR3, CFTR, PAQR5, BNIP3, GOLM1, PLA2G10, KCNK5, MLSTD1, slc16a7, NFE2L2, CGNL1, CALML4, ACSL5, KRT8, TMC7, FAT, CES3, SLAC7A7, REG4, CATSPERB, TSPAN3, SLC37A1, GPRC5A, GPT2, PAIP2B, TRIM29, IL18, HSD17B11, GSDML, TACSTD1, HSD17B2, KRT7, CLIC6, ATP2C2, HEPH, TPD52L1, HOXB6, PLS1, IL1RN, NT5E, CAB39L, S100A14, GDA, TRIM31, ARPC1B, SLC16A1, TMC5, CPEB2, LOC93432, FS, VLDLR, GCNT3, MBOAT2, CPS1, GALM, DGKD, FAM102B, LYN, SFN, GALNT7, EMP1, CSTB, RHOC, F1114959, SNRPN, ANKS4B, PCLKC, ADH7, LYZ, S100A16, SLC6A20, SCNN1G, HKDC1, SLC7A2, SPG20, 37681, FGFBP1, CA9, RDX,SAMD9, RDX, SAMD9, SERPINB5, NMU, CLRN3, SLC9A4, VTCN1, LOC339977, FUT9, GALNT5, NR5A2, OLFM4, LY75, SCPEP1, TACSTD2, MYO1A, BTNL8, VIL1, SLC28A2, DPP4, AZGP1, CDH17, NPNT, ALDH1AI, ATP13A4, ATP7B, IL2RG, POSTN, FCGBP, GPA33, DSC2, COL6A3, VNN1, SLP1, AIM1, PRKAA2, GUCY2C, P13, TIMP1, APOL1, ANPEP, SLC34A2, DMBT1, RGS2, PAPSS2, BCM01, ADH6, TM4SF20, CHST5, HHLA2, FABP1, SNORD116-21, MYO7B, MIA, MEP1A, SLC3AI, PLACE, TFPI, PGC, MUC2, LIPF, FABP2, SI, SLC17A4, GSTA1, PDZK1, RAB3B, REGIA, SPINK4, CXCL1, GKN1, BTNL3, ADH4, ALDOB, CXCL2, SLC263, MMPI, UPK1B, MEP1B, CA1, and PRSS7.

13. A method for aiding a diagnosis of Barrett's esophagus or Barrett's associated dysplasia in a subject, the method comprising collecting cells from a surface of an esophagus of the subject with a device according to claim 1 and assaying the cells for a cellular marker, wherein detection of such a marker indicates increased likelihood of a presence of Barrett's esophagus or Barrett's associated dysplasia.

14. The method of claim 13, wherein the cellular marker is selected from the group consisting of Mcm2 and TFF3.

15. The method of claim 13, wherein the cellular marker is selected from the group consisting of ABP1, DCC, HOX C10, KCNE3, LAMC2m MUC13, MUC17, NMUR2, PICR, TCPAN1, and HOXB5.

16. The method of claim 13, wherein the cellular marker is selected from the group consisting of RNF217, CCL28, AGR3, CFTR, PAQR5, BNIP3, GOLM1, PLA2G10, KCNK5, MLSTD1, slc16a7, NFE2L2, CGNL1, CALML4, ACSL5, KRT8, TMC7, FAT, CES3, SLAC7A7, REG4, CATSPERB, TSPAN3, SLC37A1, GPRC5A, GPT2, PAIP2B, TRIM29, IL18, HSD17B11, GSDML, TACSTD1, HSD17B2, KRT7, CLIC6, ATP2C2, HEPH, TPD52L1, HOXB6, PLS1, URN, NT5E, CAB39L, S100A14, GDA, TRIM31, ARPCIB, SLC16A1, TMC5, CPEB2, LOC93432, FS, VLDLR, GCNT3, MBOAT2, CPS1, GALM, DGKD, FAM102B, LYN, SFN, GALNT7, EMP1, CSTB, RHOC, FLJ14959, SNRPN, ANKS4B, PCLKC, ADH7, LYZ, S100A16, SLC6A20, SCNN1G, HKDC1, SLC7A2, SPG20, 37681, FGFBP1, CA9, RDX, SAMD9, RDX, SAMD9, SERPINB5, NMU, CLRN3, SLC9A4, VTCN1, LOC339977, FUT9, GALNT5, NR5A2, OLFM4, LY75, SCPEPI, TACSTD2, MYO1A, BTNL8, VIL1, SLC28A2, DPP4, AZGP1, CDH17, NPNT, ALDH1A1, ATP13A4, ATP7B, IL2RG, POSTN, FCGBP, GPA33, DSC2, COL6A3, VNN1, SLP1, AIM1, PRKAA2, GUCY2C, P13, TIMP1, APOL1, ANPEP, SLC34A2, DMBT1, RGS2, PAPSS2, BCM01, ADH6, TM4SF20, CHST5, HHLA2, FABP1, SNORD1 16-21, MYO7B, MIA, MEP1A, SLC3AI, PLAC8, TFPI, PGC, MUC2, LIPF, FABP2, SI, SLC17A4, GSTA1, PDZK1, RAB3B, REG1A, SPINK4, CXCL1, GKN1, BTNL3, ADH4, ALDOB, CXCL2, SLC26A3, MMPI, UPK1B, MEP1B, CA1, and PRSS7.

* * * * *